United States Patent

Nagamura et al.

Patent Number: 6,004,801
Date of Patent: *Dec. 21, 1999

[54] METHOD OF PURIFYING K-252A

[75] Inventors: Satoru Nagamura; Mitsutaka Kino; Tadashi Kinoshita, all of Yamaguchi, Japan

[73] Assignee: Kyowa Hakko Kogyo Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/973,127

[22] PCT Filed: Apr. 2, 1997

[86] PCT No.: PCT/JP97/01134

§ 371 Date: Dec. 3, 1997

§ 102(e) Date: Dec. 3, 1997

[87] PCT Pub. No.: WO97/38120

PCT Pub. Date: Oct. 16, 1997

[30] Foreign Application Priority Data

Apr. 9, 1996 [JP] Japan ................................ 8-086469

[51] Int. Cl.[6] .................................................. C12P 17/18
[52] U.S. Cl. ........................... 435/267; 435/119; 435/800
[58] Field of Search ................................... 435/119, 267; 438/800

[56] References Cited

U.S. PATENT DOCUMENTS 4,555,402  11/1985  Matsuda et al. ...................... 424/122

FOREIGN PATENT DOCUMENTS 41489  of 1985  Japan .

OTHER PUBLICATIONS

Ross et al. "Differential Biological Effects of K252 Kinase Inhibitors are related to Membrane Solubility but not to Permeability" J. Neurocehm 65 No. 6 (1995) pp. 2748–2756.

Wood et al., "Design and Implementation of an Efficient Synthetic Approach to Furanosylated Indolocarbazoles: Total Synthesis of (+)–and(–)–K252A," *J. Am. Chem. Soc.* 119: 9641–9651 (1997).

Kase et al., "K–252a, a potent inhibitor of protein kinase C from microbial orgin," *J. Antibiot.* 39: 1059–1065 (1986).

Yasuzawa et al., "The structures of the novel protein kinase C inhibitors K–252a, b, c and d," *J. Antibiot.* 39: 1072–1078 (1986).

Nakanishi et al., "K–252 b, c, and d, potent inhibitors of protein kinase C from microbial orgin," *J. Antibiot.* 39: 1066–1071 (1986).

Lazarovici et al., "K–252a inhibits the increase in c–fos transcription and the increase in intracellular calcium produced by nerve growth factor in PC12 cells," *J. Neurosci. Res.* 23: 1–8 (1989).

Nakayama et al., "K252a inhibits the phosphorylation of pRb without changing the levels of G1 cyclins and Cdk2 protein in human hepatoma cells," *Biochem. Biophys. Res. Commun.* 224: 180–183 (1996).

Isono et al., "Epidermal growth factor induces PC12 cell differentiation in the presence of the protein kinase inhibitor K–252a," *J. Neurochem.* 4: 1235–1245 (1994).

Gschwendt et al., "Differentiative action of K252a on protein kinase C and a calcium–unresponsive, phorbol ester/phospholipid–activated protein kinase," *Biochem. Res. Commun.* 164: 974–982 (1989).

*Primary Examiner*—Herbert J. Lilling
*Attorney, Agent, or Firm*—Medlen & Carroll, LLP

[57] ABSTRACT

The present invention provides a purification process of K-252a, which comprises:

treating microorganism cells containing K-252a represented by formula (I):

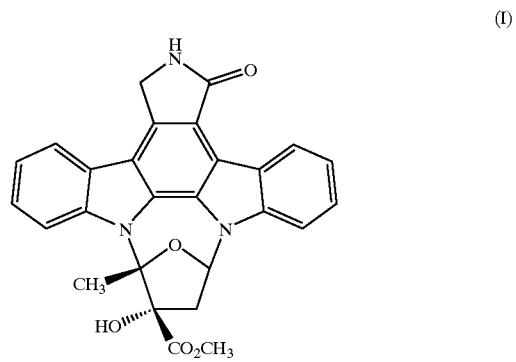

(I)

with an alkaline solution to convert K-252a into K-252b represented by formula (II):

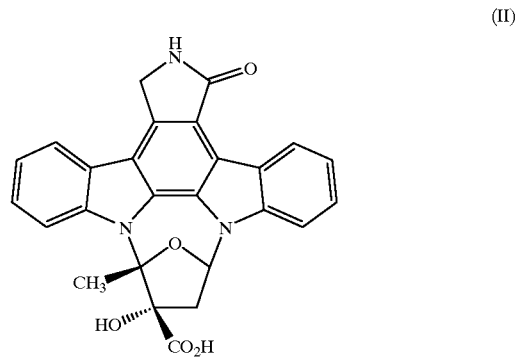

(II)

or alkali salts thereof, which are then released out of the cells, methylating K-252b or alkali salts thereof to convert them into K-252a again, and isolating and collecting the resulting K-252a.

2 Claims, No Drawings

METHOD OF PURIFYING K-252A

TECHNICAL FIELD

The present invention relates to a purification process of K-252a.

BACKGROUND ART

K-252a is a physiologically active substance produced by microorganisms (Japanese Patent Laid-Open Application No. 41489/1985). It has an inhibition activity for protein kinase C and exhibits various pharmacological effects.

A conventional purification process of K-252a comprises the steps of: a) collecting microorganisms by filtering a culture solution; b) extracting the microorganisms by adding thereto a hydrous or anhydrous organic solvent such as methanol or acetone; c) removing the microorganisms by filtration; d) concentrating the resulting extracted solution; e) further extracting it with an anhydrous organic solvent in high yields; f) separating it by using a column filled with adsorbents such as active carbon or Diaion HP-10 and carriers such as silica gel, silanized silica gel, aluminum oxide or dextran; and g) concentrating it to obtain a crude K-252a crystal. However, the crystal thus obtained will not have sufficient purity. This process therefore further needs a recrystallization step in order to achieve higher purity. Furthermore, this process is not suitable for filtering a large amount of the culture solution because it is considerably difficult to filter the culture solution in this process.

Alternatively, it is also possible to collect an extracted solution by directly extracting a culture solution with an organic solvent and then filtering it. However, this process further needs a column treatment because the organic solvent used for extraction should be added in the same volume as the culture solution or more due to a lower solubility of K-252a in various solvents (5 to 10 g/l, for example 5 g/l in acetone), a liquid volume to be treated is extremely increased and the resulting extracted solution has lower purity.

DISCLOSURE OF THE INVENTION

The present invention provides a purification process of K-252a, which comprises:

treating microorganism cells containing K-252a represented by formula (I):

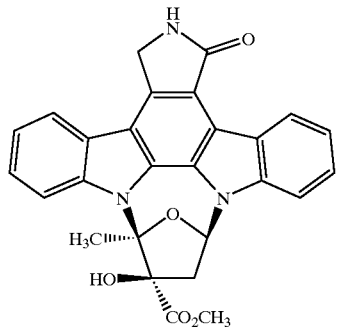

with an alkaline solution to convert K-252a into K-252b represented by formula (II):

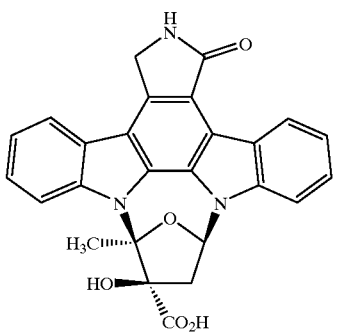

or alkali salts thereof, which are then released out of the cells, methylating K-252b or alkali salts thereof to convert them into K-252a again, and isolating and collecting the resulting K-252a.

The microorganism cells containing K-252a used in the present invention may be obtained by culturing microorganisms capable of producing K-252a in a nutrient medium.

The microorganisms capable of producing K-252a include Nocardiopsis sp. K-252 deposited at the Agricultural Research Service Culture Collection in the United States under accession number NRRL15532 (Japanese Patent Laid-Open Application No. 41489/1985).

As the nutrient medium any conventional medium may be used which is generally used for culturing microorganisms capable of producing K-252a. Examples include a nutrient medium used for culturing normal antinomycetes. The microorganisms may be suitably cultured in a liquid medium, particularly under a submerged culture condition. They may be preferably cultured at a temperature of 25 to 40° C. and at a neutral pH of 5 to 9, more preferably 6 to 8.

After K-252a has been accumulated inside the microorganism cells, the culture of the cells is stopped to obtain microorganisms used for the purification of K-252a. K-252a may be preferably accumulated inside the cells at a concentration of at least 1.0 g/liter of cell volume, more preferably at least 5.0 g/liter of cell volume.

The microorganism cells can be collected, for example, by centrifugation. Preferably, an acid such as hydrochloric acid, sulfuric acid, nitric acid and acetic acid, preferably sulfuric acid, may be added to the culture solution to adjust its pH to 2–4 before collecting the cells.

Any centrifugal separator may be used for centrifugation. Particularly, Westfalia separator and α-Labal separator are preferred because they can continuously separate a large amount of the culture solution while washing the microorganism cells with washing water.

The collected cells maybe suspended into an alkaline solution at a concentration of 10 to 80% by volume, preferably 30 to 50% by volume to treat them with the alkaline solution.

An alkali used for the alkaline solution includes hydroxides, carbonates and bicarbonates of alkaline metals such as lithium, sodium or potassium, alkaline earth metals such as magnesium, calcium or barium, mono- to tri-valent metals such as aluminum, and ammonium. Examples include hydroxide such as sodium hydroxide, potassium hydroxide, magnesium hydroxide, barium hydroxide, calcium hydroxide or ammonium hydroxide, carbonates such as sodium carbonate or potassium carbonate, and bicarbonates such as sodium bicarbonate or potassium bicarbonate, hydroxides of alkaline metals being preferred. The alkaline solution has an alkali content of 0.1 to 5 N, preferably 1 to 2 N.

The alkaline treatment of the microorganism cells may be carried out, for example, by heating the cells suspended into the alkaline solution at 30 to 90° C., preferably 60 to 80° C., for 1 to 24 hours, preferably 3 to 5 hours. In this alkaline treatment, K-252a present in the cells can be hydrolyzed to K-252b or alkali salts thereof and extracted from the cells.

K-252b or alkali salts thereof extracted with the alkaline solution may be further isolated using a column filled with resins such as an adsorption resin or an ion-exchange resin with or without removal of microorganism cells. The microorganism cells may be removed, for example, by filtration using Nutsche, Kiriyama funnel, filter press or basket separator.

The adsorption resin includes SP-207, HP-20, HP-30, HP-40, HP-50 (commercially available from Mitsubishi Kasei Corporation) and XAD-2, XAD-4, XAD-284, S-30, S-37, ES-33 (commercially available from Rohm & Haas) The ion-exchange resin includes strongly basic ion-exchange resins such as PA-304, PA-412 (commercially available from Mitsubishi Chemical Corporation), IRA-410, IRA-911, A-26, ES-109, A-101D, ES-111 (commercially available from Rohm & Haas), DOWEX-2, DOWEX-4 (commercially available from Dow Chemical) and MP-500A, MP-5080 (commercially available from Bayer).

The adsorption resin or ion-exchange resin retaining K-252b or alkali salts thereof may be washed with water or hydrous organic solvents and then subjected to elution of K-252b or alkali salts thereof from the resin using organic solvents or hydrous organic solvents.

The hydrous organic solvents used for washing include water-containing polar solvents comprising acetone, methanol, ethanol, propanol or butanol. These solvents may have water content of at least 20%, preferably at least 50%.

The organic solvents used for elution include ketones such as acetone, methyl ethyl ketone or methyl isobutyl ketone, alcohols such as methanol, ethanol or butanol, and esters such as ethyl acetate or butyl acetate. The hydrous organic solvents used for elution include water-containing polar solvents comprising acetone, methanol or ethanol. These solvents may have water content of at most 20%, preferably at most 10%. To the hydrous organic solvents may be optionally added an alkali such as sodium hydroxide or a salt such as sodium chloride and ammonium chloride. The alkali may be preferably added at a concentration of 0.1 to 1.0 N and the salt may be preferably added at a concentration of 0.1 to 1.0 M.

The solution extracted with the alkaline solution or further isolated using the column, which contains K-252b or alkali salts thereof, may be concentrated without adjusting its pH or under an acidic condition by adding thereto an acid such as hydrochloric acid or sulfuric acid, until an amount of K-252b or alkali salts thereof in the solution reaches 0.5 to 20 mg/ml, preferably 5 to 10 mg/ml. Alternatively, the concentrated solution may be also prepared by adding an organic solvent to K-252b or alkali salts thereof obtained by evaporating the eluted solution to dryness. The organic solvent may be added in an amount of 50 to 2000 ml, preferably 100 to 200 ml for each gram of K-252b or alkali salts thereof. The organic solvent to be added includes the abovementioned organic solvents used for the elution of K-252b or alkali salts thereof.

K-252b or alkali salts thereof may be converted into K-252a again by methylating them.

The methylation of K-252b or alkali salts thereof may be carried out by adding a methylating agent such as dimethyl sulfate to the above concentrated solution in an amount of 1 to 20 equivalents, preferably 2 to 3 equivalents for each equivalent of K-252b or alkali salts thereof, and reacting them under heating at 50 to 100° C., preferably 60 to 80° C., for 2 to 36 hours, preferably 6 to 12 hours.

Alternatively, it is also possible to carry out the methylation of K-252b or alkali salts thereof as follows. To each liter of the above concentrated solution are added 100 to 2000 ml, preferably 500 to 800 ml of methanol and an inorganic acid such as hydrochloric acid or sulfuric acid, an organic acid such as methanesulfonic acid or toluenesulfonic acid, or a cation-exchange resin such as SK-1A, SK-1B, SK-116 (commercially available from Mitsubishi Chemical Corporation), IR-120B, IR-200 (commercially available Rohm & Haas) or DOWEX-50W (commercially available from Dow Chemical). Next, they are reacted each other under heating at 50 to 100° C., preferably 60 to 80° C., for 2 to 36 hours, preferably 6 to 12 hours. The inorganic acid, organic acid or cation-exchange resin may be respectively used in an amount of 1 to 20 equivalents, preferably 2 to 3 equivalents for each equivalent of K-252b or alkali salts thereof.

The reaction solution thus methylated may be concentrated under vacuum and cooled to precipitate K-252a The concentration under vacuum may be carried out at a pressure of 700 to 760 mmHg, preferably 720 to 760 mmHg and at a temperature of 30 to 80° C., preferably 40 to 50° C. until the concentration of K-252a reaches a saturated concentration or less. K-252a may be preferably precipitated at a temperature of 10 to 60° C.

Alternatively, it is also possible to precipitate K-252a from the reaction solution by evaporating the methylated solution to dryness and adding thereto water and an organic solvent- Water may be preferably added in an amount of 0.01 to 1 times, more preferably 0.1 to 0.5 times the volume of the organic solvent used in the methylation. The organic solvent used for the precipitation of K-252a includes any water-miscible organic solvent mentioned above and may be preferably added in an amount of 0.5 to 1.5 times the volume of water added.

The precipitated K-252a can be isolated and collected in a general manner, for example, by filtration and drying.

The present invention will be further illustrated by the following test examples.

TEST EXAMPLES

Test Example 1

Nocardiopsis sp. K-252 (NRRL15532) was used as seed cells. A culture medium comprising the following ingredients was used as a first culture medium (pH 7.2 to 7.4 before sterilized):

| | |
|---|---|
| Glucose | 0.5 g/dl |
| Soluble Starch | 3 g/dl |
| Soy Bean Meal | 3 g/dl |
| Corn Steep Liquor | 0.5 g/dl |
| Yeast Extract | 0.5 g/dl |
| Calcium Carbonate | 0.3 g/dl. |

One platinum loop of the seed cells was inoculated into a thick test tube (50 ml volume) containing 14 ml of the first culture medium and incubated at 30° C. for 3 days under a shaken culture condition.

An Erlenmeyer flask (300 ml volume) containing 40 ml of a second culture medium was inoculated with 4 ml of this first culture solution and incubated at 30° C. for 3 days under a shaken culture condition. The second culture medium comprises the same ingredients as the first culture medium.

A baffled Erlenmeyer flask (2 liter volume) containing 300 ml of a third culture medium was inoculated with 40 ml of this second culture solution and incubated at 30° C. for 4 days under a shaken culture condition. The third culture medium comprises the same ingredients as the second culture medium. A stainless jar fermentor (30 liter volume) containing 16 liters of a main culture medium for fermentation was inoculated with 900 ml of this third culture solution and incubated at 30° C. for 7 days under an aeration-agitation culture condition at an agitation rate of 300 rpm and at an aeration rate of 16 liters/minute. The main culture medium for fermentation comprises the same ingredients as the first culture medium.

One liter of this main culture solution was adjusted to pH 3 with concentrated sulfuric acid, and the microorganism cells (300 ml) were collected using a high-speed cooling centrifugal separator (CR-20, Hitachi). Two grams of K-252a in total were contained in 300 ml of the cells. These cells were washed by adding thereto 600 ml of water and then centrifuging them again.

The microorganism cells thus obtained were adjusted to pH 12 by adding sodium hydroxide, and then heated at 80° C. for 3 hours to extract K-252a. The resulting cell suspension was adjusted to pH 7 with concentrated sulfuric acid, and then filtered by Nutsche to remove the cells.

K-252a present in the extracted solution thus obtained was almost completely converted into K-252b or alkali salts thereof.

On the contrary, when acetone is used for extraction, 10 liters of acetone were required to extract K-252a from 300 ml of the cells in an 80% yield.

In the present invention, K-252a can be almost completely extracted from the microorganism cells without using organic solvents by converting K-252a into K-252b or alkali salts thereof.

BEST MODES FOR CARRYING OUT THE INVENTION

Example 1

The procedure of Test Example 1 was repeated to prepare a culture solution. One liter of the resulting culture solution was adjusted to pH 3 with concentrated sulfuric acid, and the microorganism cells (300 ml) were collected using a high-speed cooling centrifugal separator (CR-20, Hitachi). Two grams of K-252a were contained in 300 ml of these cells. These cells were washed again by centrifugation. To these washed cells was added 600 ml of water to obtain a cell suspension.

The resulting cell suspension was adjusted to pH 12 by adding concentrated sodium hydroxide, and then heated at 80° C. for 3 hours to extract K-252a. The cell suspension treated under heating was adjusted to pH 7 with concentrated sulfuric acid, and then filtered by Nutsche to remove the cells. The extracted solution thus obtained was applied to an adsorption resin (200 ml volume, SP-207, Mitsubishi Chemical Corporation) at a flow rate of SV2. The adsorption resin was washed with 200 ml of water and 400 ml of 50% methanol, and then subjected to elution using 2000 ml of 100% methanol. A fraction containing K-252b or alkali salts thereof was concentrated to 1000 ml.

To this eluted solution was added 1 ml of concentrated sulfuric acid and then heated at 60° C. for 3 hours to convert K-252b or alkali salts thereof into K-252a. The resulting solution was cooled and filtered to obtain a crude K-252a crystal with 75% purity in a 70% yield (1.4 g as a pure crystal). The resulting crude K-252a crystal can be easily further purified by conventional recrystallization to obtain K-252a with 95% purity in an 80% yield (1.1 g as a pure crystal).

Example 2

The procedure of Example 1 was repeated to treat the microorganism cells with sodium hydroxide, to apply the resulting extracted solution to the adsorption resin and to wash the adsorption resin. K-252b or alkali salts thereof adsorbed to the resin were eluted with 9:1 methanol-sodium hydroxide. The resulting solution eluted from the resin was evaporate to dryness, and then dissolved into 1000 ml of acetone. Two equivalents of dimethyl sulfate were added to this solution and heated at 60° C. for 3 hours to convert K-252b or alkali salts thereof into K-252a. The resulting solution was cooled and filtered to obtain a crude K-252a crystal with 75% purity in a 70% yield (1.4 g as a pure crystal). The resulting crude K-252a crystal can be easily further purified by conventional recrystallization to obtain K-252a with 95% purity in an 80% yield (1.1 g as a pure crystal).

Example 3

The procedure of Example 1 was repeated to treat the microorganism cells with sodium hydroxide. The treated cells were then directly applied to an adsorption resin without isolating K-252b or alkali salts thereof from the cells. Next, the procedure of Example 2 was repeated to obtain a crude K-252a crystal with 75% purity in a 70% yield (1.4 g as a pure crystal). The resulting crude K-252a crystal can be easily further purified by conventional recrystallization to obtain K-252a with 95% purity in an 80% yield (1.1 g as a pure crystal).

Example 4

The procedure of Example 2 was repeated to obtain a crude K-252a crystal with 75% purity in a 70% yield (1.4g as a pure crystal), except that a strongly basic ion-exchange resin (PA-412, Mitsubishi Chemical Corporation) was used instead of the adsorption resin and 9:1 methanol-0.1 N ammonium chloride was used as an eluent. The resulting crude K-252a crystal can be easily further purified by conventional recrystallization to obtain K-252a with 95% purity in an 80% yield (1.1 g as a pure crystal).

Example 5

The procedure of Example 4 was repeated to obtain a crude K-252a crystal with 75% purity in a 70% yield (1.4g as a pure crystal), except that the microorganism cells were directly applied to the ion-exchange resin without isolating K-252b or alkali salts thereof from the cells. The resulting crude K-252a crystal can be easily further purifiedby conventional recrystallization to obtain K-252a with 95% purity in an 80% yield (1.1 g as a pure crystal).

INDUSTRIAL APPLICABILITY

According to the present invention, the industrial purification of K-252a can be easily and inexpensively achieved without using a large amount of organic solvents. K-252a obtained according to the present invention has higher purity.

What is claimed is:

1. A purification process of K-252a which comprises:
   treating microorganism cells containing K-252a represented by formula (I):

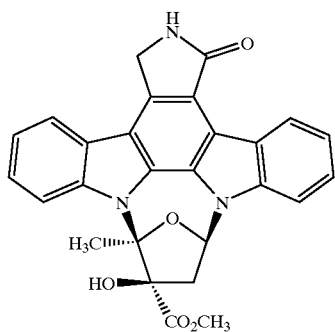

(I)

with an alkaline solution to convert K-252a into K-252b represented by formula (II):

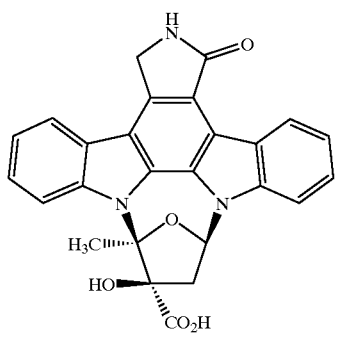

(II)

or alkali salts thereof, which are then released out of the cells, methylating K-252b or alkali salts thereof to convert them into K-252a again, and isolating and collecting the resulting K-252a.

2. A purification process of K-252a which comprises:

treating micoorganism cells containing K-252a represented by formula (I):

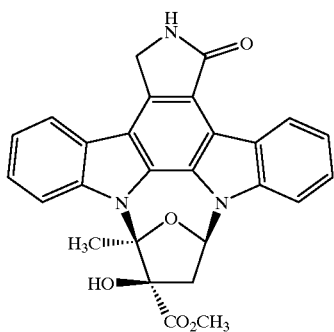

(I)

with an alkaline solution to convert K-252a into K-252b represented by formula (II):

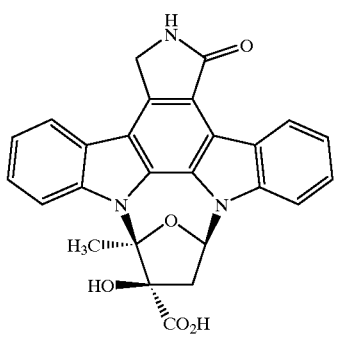

(II)

or alkali salts thereof, which are then released out of the cells, isolating K-252b or alkali salts thereof, methylating K-252b or alkali salts thereof to convert them into K-252a again, and isolating and collecting the resulting K-252a.

* * * * *